(12) United States Patent
Moradi et al.

(10) Patent No.: US 8,436,211 B2
(45) Date of Patent: May 7, 2013

(54) TETRAARYLBORATE PROCESS FOR THE PREPARATION OF SUBSTITUTED BIPHENYLS

(75) Inventors: Wahed Ahmed Moradi, Monheim (DE); Norbert Lui, Odenthal (DE); Michael Dockner, Köln (DE); Thomas Jagusch, Kranenburg (DE)

(73) Assignee: Bayer CropScience AG, Monheim (DE)

( * ) Notice: Subject to any disclaimer, the term of this patent is extended or adjusted under 35 U.S.C. 154(b) by 182 days.

(21) Appl. No.: 12/871,374

(22) Filed: Aug. 30, 2010

(65) Prior Publication Data
US 2011/0105796 A1 May 5, 2011

Related U.S. Application Data

(60) Provisional application No. 61/239,516, filed on Sep. 3, 2009.

(30) Foreign Application Priority Data

Aug. 31, 2009 (EP) .................................. 09169039

(51) Int. Cl.
*C07C 233/05* (2006.01)
(52) U.S. Cl.
USPC ............................................. 564/221; 568/6
(58) Field of Classification Search .................. 564/221; 568/6
See application file for complete search history.

(56) References Cited

U.S. PATENT DOCUMENTS

| 6,740,724 | B2 * | 5/2004 | Wang et al. ................... 526/347 |
| 7,772,446 | B2 | 8/2010 | Engel et al. |
| 2008/0183021 | A1 | 7/2008 | Engel et al. |
| 2010/0185015 | A1 | 7/2010 | Straub et al. |
| 2011/0003999 | A1 | 1/2011 | Dockner |
| 2011/0092736 | A1 | 4/2011 | Dockner |

FOREIGN PATENT DOCUMENTS

JP 2008-63329 * 3/2008

OTHER PUBLICATIONS

Bellina, F., et al., "Palladium Catalysts for the Suzuki Cross-Coupling Reaction: An Overview of Recent Advances," *Synthesis* 15:2419-2440, Thieme Stuttgart, United States (2004).

Littke, A.F. & Fu, G.C., "Palladiumkatalysierte Kupplungen von Arylchloriden," *Angew. Chem.* 114:4350-4386, Wiley-VCH, Germany (2002).

Lu, G., et al., "Palladium charcoal-catalyzed, ligandless Suzuki reaction by using tetraarylborates in water," *Tet. Lett.* 46:4255-4259, Elsevier Ltd., United Kingdom (2005).

Miyaura, N. & Suzuki, A., "Palladium-Catalyzed Cross-Coupling Reactions of Organoboron Compounds," *Chem. Rev.* 95:2457-2483, American Chemical Society, United States (1995).

* cited by examiner

*Primary Examiner* — Shailendra Kumar
(74) *Attorney, Agent, or Firm* — Sterne, Kessler, Goldstein & Fox P.L.L.C.

(57) ABSTRACT

The present invention relates to a process for the preparation of substituted biphenyls by reacting aryl halides with tetraarylborates in the presence of palladium catalysts.

15 Claims, No Drawings

TETRAARYLBORATE PROCESS FOR THE PREPARATION OF SUBSTITUTED BIPHENYLS

This application claims benefit of 61/239,516, filed Sep. 3, 2009.

The present invention relates to a process for the preparation of substituted biphenyls by reacting aryl halides with tetraarylborates in the presence of palladium catalysts.

Biaryl compounds, in particular biphenyl compounds, are of industrial importance as fine chemicals, intermediates for drugs, optical brighteners and agrochemicals.

A frequently used method for the synthesis of biphenyls on the laboratory scale is the Suzuki reaction, in which iodo- or bromoaromatics and, in exceptional cases, chloroaromatics are reacted with aryl-, vinyl- or alkylboronic acid derivatives in the presence of palladium catalysts. Review articles which describe this method are to be found, for example, in N. Miyaura, A. Suzuki, *Chem. Rev.* 1995, 95, 2457 and Bellina, F. et al. *Synthesis* 2004, 2419. A review of the use of trialkylphosphine ligands in the Pd-catalyzed reaction of chloroaromatics is to be found in Littke, A. F. & Fu, G. C. *Angew. Chem.* 2002, 114, 4350.

In the Suzuki couplings described in the prior art, arylboronic acids are frequently used as coupling components. These have the disadvantage that only one aryl radical can be transferred with each equivalent of the arylboronic acid used.

In all processes described in the prior art, palladium complexes which are expensive or complicated to prepare are used or it is necessary to work in the presence of an excess of arylboronic acid in order to achieve a good yield. This increases the costs of the process not only through the loss of valuable arylboronic acid but also through more complicated cleaning and isolation processes which are necessary in order to separate off excess boronic acid and by-products formed therefrom, such as deboronated aromatics and homocoupling products.

WO 2006/092429 describes the reaction of aromatic borinic acids with aryl halides in aqueous solvent systems, inter alia in the presence of trialkylphosphines. However, the fact that borinic acids cannot be readily synthesized in all cases and that the reactivity is substantially poorer than that of the corresponding boronic acids appears to be a disadvantage of this process. Moreover, in the case of the borinic acids, there is furthermore the desire to increase the number of transferable aryl radicals.

G. Lu et al. in *Tetrahedron Letters* 2005, 46, 4255-4259, describe the use of sodium tetraphenylborates and sodium tetratolylborates as stable and commercially available borate sources.

WO 2009/003650 teaches that the course of the Suzuki reaction is also decisively influenced by the reactivity of the boronic acid or borinic acid used, in particular aromatics deactivated by electron-attracting substituents being capable of reacting more slowly and of giving homocoupling products. However, scarcely any attention is paid to this problem in the literature since a large excess of boronic acid is generally employed here and the yields are based only on the conversion of the haloaromatics.

A further disadvantage of the processes already described in the prior art is therefore the competing homocoupling reaction of the haloaromatics with formation of toxic polyhalogenated biphenyls.

Electron-poor tetraarylborates are therefore considered to be not very reactive and therefore unsuitable in Suzuki couplings.

The first object of the present invention is to improve the space-time yield of the Suzuki coupling.

A further object of the present invention is to provide a novel process for the preparation of electron-poor biphenyls, in particular of those which are substituted by a plurality of halogen atoms (2, 3 or 4 halogen atoms), which does not have the disadvantages of the known processes. The process should be suitable for being carried out on an industrial scale and should give electron-poor biphenyls in high yield and purity with optimum catalyst productivity.

This object is achieved by a process for the preparation of substituted biphenyls of the formula (I)

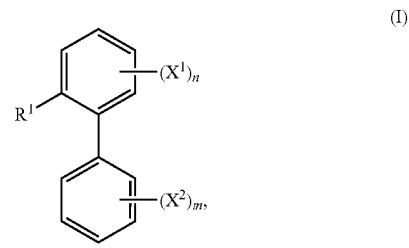

in which $X^1$ and $X^2$, independently of one another, are selected from halogen atoms and linear or branched $C_{1-12}$-alkyl groups;

n is 0, 1 or 2;

m is 1, 2, 3, 4 or 5;

$R^1$ is selected from the group consisting of amino ($NHR^2$), nitro ($NO_2$), amide groups ($R^2$—(CO)—NH—) or Schiff's bases ($R^3R^4C=N$—), $R^2$, $R^3$ and $R^4$ are selected from linear or branched $C_{1-12}$-alkyl groups or cyclic $C_{3-8}$-alkyl groups, benzyl groups, benzoyl groups, pyrazolyl groups of the formula (Ia), pyridyl groups of the formula (Ib)

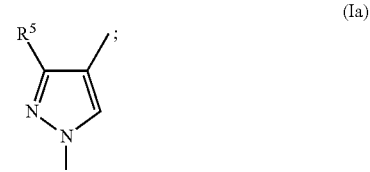

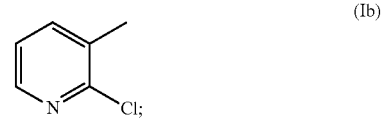

$R^5$ is a linear or branched $C_{1-12}$-alkyl group or a $C_{1-6}$-haloalkyl group having 1 to 6 halogen atoms;

by reacting aryl halides of the formula (II)

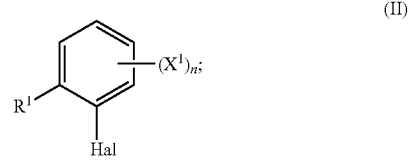

in which
Hal is selected from bromine, chlorine and iodine,
$R^1$, $X^1$ and n correspond to the above definitions;
in the presence of a base and of a palladium catalyst in a solvent,
with tetraarylborates of the formula (III)

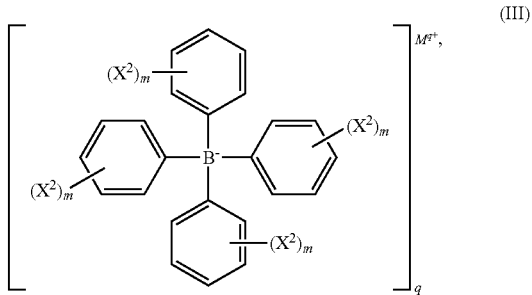

in which
$X^2$ and m correspond to the above definitions and
$M^{q+}$ is a cation which is selected from ammonium, alkali metal (q=1) and alkaline earth metal cations (q=2).

The process according to the invention preferably permits the coupling of all 4 aryl radicals of the tetraarylborate (III) to the aryl halides of the formula (II). It therefore improves the space-time yield of the Suzuki coupling.

In the context of the present invention, the term halogens (X), unless defined otherwise, comprises those elements which are selected from the group consisting of fluorine, chlorine, bromine and iodine, fluorine, chlorine and bromine being preferably used and fluorine and chlorine particularly preferably used.

Optionally substituted groups may be mono- or polysubstituted, it being possible for the substituents to be identical or different in the case of polysubstitutions.

Alkyl groups substituted by one or more halogen atoms (—X) are, for example, selected from trifluoromethyl ($CF_3$), difluoromethyl ($CHF_2$), $CF_3CH_2$, $ClCH_2$, $CF_3CCl_2$.

In the context of the present invention, unless defined otherwise, alkyl groups are linear or branched hydrocarbon groups which may optionally have one, two or more heteroatoms which are selected from O, N, P and S. Moreover, the alkyl groups according to the invention may optionally be substituted by further groups which are selected from —R', halogen (—X), alkoxy (—OR'), thioether or mercapto (—SR'), amino (—NR'$_2$), silyl (—SiR'$_3$), carboxyl (—COOR'), cyano (—CN), acyl (—(C=O)R') and amide groups (—CONR$_2$'), in which R' is hydrogen or a $C_{1-12}$-alkyl group, preferably $C_{2-10}$-alkyl group, particularly preferably $C_{3-8}$-alkyl group, which may have one or more heteroatoms selected from N, O, P and S.

The definition $C_1$-$C_{12}$-alkyl comprises the largest range defined herein for an alkyl group. Specifically, this definition comprises, for example, the meanings methyl, ethyl, n-propyl, isopropyl, n-butyl, isobutyl, sec-butyl and tert-butyl, n-pentyl, n-hexyl, 1,3-dimethylbutyl, 3,3-dimethylbutyl, n-heptyl, n-nonyl, n-decyl, n-undecyl, n-dodecyl.

In the context of the present invention, unless defined otherwise, cycloalkyl groups are annular hydrocarbon groups which may optionally have one, two or more heteroatoms which are selected from O, N, P and S. Moreover, the cycloalkyl groups according to the invention may optionally be substituted by further groups which are selected from —R', halogen (—X), alkoxy (—OR'), thioether or mercapto (—SR'), amino (—NR'$_2$), silyl (—SiR'$_3$), carboxyl (—COOR'), cyano (—CN), acyl (—(C=O)R') and amide groups (—CONR$_2$'), in which R' is hydrogen or a $C_{1-12}$-alkyl group, preferably $C_{2-10}$-alkyl group, particularly preferably $C_{3-8}$-alkyl group, which may have one or more heteroatoms selected from N, O, P and S.

The definition $C_3$-$C_8$-cycloalkyl comprises the largest range defined herein for a cycloalkyl group. Specifically, this definition comprises, for example, the meanings cyclopropyl, cyclobutyl, cyclohexyl, cycloheptyl and cyclooctyl.

In the context of the present invention, unless defined otherwise, aryl groups are aromatic hydrocarbon groups which may have one, two or more heteroatoms which are selected from O, N, P and S and may optionally be substituted by further groups which are selected from —R', halogen (—X), alkoxy (—OR'), thioether or mercapto (—SR'), amino (—NR'$_2$), silyl (—SiR'$_3$), carboxyl (—COOR'), cyano (—CN), acyl (—(C=O)R') and amide groups (—CONR$_2$'), in which R' is hydrogen or a $C_{1-12}$-alkyl group, preferably $C_{2-10}$-alkyl group, particularly preferably $C_{3-8}$-alkyl group, which may have one or more heteroatoms selected from N, O, P and S.

The definition $C_{5-18}$-aryl comprises the largest range defined herein for an aryl group having 5 to 18 skeletal atoms, it being possible for the C atoms to be exchanged for heteroatoms. Specifically, this definition comprises, for example, the meanings cyclopentadienyl, phenyl, cycloheptatrienyl, cyclooctatetraenyl, naphthyl and anthracenyl; 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl; 1-pyrrolyl, 1-pyrazolyl, 1,2,4-triazol-1-yl, 1-imidazolyl, 1,2,3-triazol-1-yl, 1,3,4-triazol-1-yl; 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

In the context of the present invention, unless defined otherwise, arylalkyl groups (aralkyl groups) are alkyl groups which are substituted by aryl groups and which may have a $C_{1-8}$-alkylene chain and may be substituted in the aryl skeleton or the alkylene chain by one or more heteroatoms which are selected from O, N, P and S and optionally by further groups which are selected from —R', halogen (—X), alkoxy (—OR'), thioether or mercapto (—SR'), amino (—NR'$_2$), silyl (—SiR'$_3$), carboxyl (—COOR'), cyano (—CN), acyl (—(C=O)R') and amide groups (—CONR$_2$'), in which R' is hydrogen or a $C_{1-12}$-alkyl group, preferably $C_{2-10}$-alkyl group, particularly preferably $C_{3-8}$-alkyl group, which may have one or more heteroatoms selected from N, O, P and S.

The definition $C_{7-19}$-aralkyl group comprises the largest range defined herein for an arylalkyl group having altogether 7 to 19 atoms in the skeleton and alkylene chain. Specifically, this definition comprises, for example, the meanings benzyl and phenylethyl.

In the context of the present invention, unless defined otherwise, alkylaryl groups (alkaryl groups) are aryl groups which are substituted by alkyl groups and which may have a $C_{1-8}$-alkylene chain and may be substituted in the aryl skeleton or the alkylene chain by one or more heteroatoms which are selected from O, N, P and S and optionally by further groups which are selected from —R', halogen (—X), alkoxy (—OR'), thioether or mercapto (—SR'), amino (—NR'$_2$), silyl (—SiR'$_3$), carboxyl (—COOR'), cyano (—CN), acyl (—(C═O)R') and amide groups (—CONR$_2$'), in which R' is hydrogen or a C$_{1-12}$-alkyl group, preferably C$_{2-10}$-alkyl group, particularly preferably C$_{3-8}$-alkyl group, which may have one or more heteroatoms selected from N, O, P and S.

The definition C$_{7-19}$-alkylaryl group comprises the largest range defined herein for an alkylaryl group having altogether 7 to 19 carbon atoms in the skeleton and alkylene chain. Specifically, this definition comprises, for example, the meanings tolyl, 2,3-, 2,4-, 2,5-, 2,6-, 3,4- or 3,5-dimethylphenyl.

The alkyl, alkenyl, alkinyl, aryl, alkaryl and aralkyl groups can moreover have one or more heteroatoms which—unless defined otherwise—are selected from N, O, P and S. The heteroatoms replace the numbered carbon atoms. The compounds according to the invention may optionally be present as mixtures of different possible isomeric forms, in particular of stereoisomers, such as, for example, E- and Z-, threo- and erythro-, and optical isomers, but optionally also of tautomers. Both the E- and the Z-isomers as well as the threo- and erythro- and the optical isomers, any desired mixtures of these isomers and the possible tautomeric forms are disclosed and claimed.

In a preferred embodiment of the process according to the invention for the preparation of substituted biphenyls of the formula (I), the substituents are defined as follows:
X$^1$ is 5-fluoro;
X$^2$ is 3/4-chloro;
n is 1;
m is 2;
R$^1$ is selected from the group consisting of amino (NH$_2$), nitro (NO$_2$), amide groups (R$^2$—(CO)—NH—) or Schiff's bases (R$^3$R$^4$C═N—),
R$^2$, R$^3$ and R$^4$ are selected from linear or branched C$_{1-12}$-alkyl groups or cyclic C$_{3-8}$-alkyl groups.

In a further preferred embodiment of the process according to the invention for the preparation of substituted biphenyls of the formula (I), the substituents are defined as follows:
X$^1$ is hydrogen;
X$^2$ is 3,4,5-fluoro;
n is 1;
m is 3;
R$^1$ is selected from the group consisting of amino (NH$_2$), nitro (NO$_2$), amide groups (R$_2$—(CO)—NH—) or Schiff's bases (R$^3$R$^4$C═N—),
R$^2$, R$^3$ and R$^4$ are selected from linear or branched C$_{1-12}$-alkyl groups or cyclic C$_{3-8}$-alkyl groups.

In the context of the present invention, the aryl halides of the formula (II) are chloro-, bromo- or iodoaromatics.

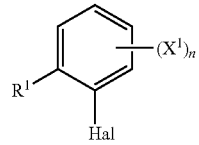

(II)

In formula (II),
X$^1$ is selected from halogen atoms and linear or branched C$_{1-12}$-alkyl groups, preferably 5-fluoro;
n is 0, 1 or 2, preferably 0 or 1;
R$^1$ is selected from the group consisting of amino (NHR$^2$), nitro (NO$_2$), amide groups (R$^2$—(CO)—NH—) or Schiff's bases (R$^3$R$^4$C═N—), preferably from amino and nitro groups;
R$^2$, R$^3$ and R$^4$ are selected from linear or branched C$_{1-12}$-alkyl groups or cyclic C$_{3-8}$-alkyl groups, benzyl groups, benzoyl groups, pyrazolyl groups of the formula (Ia), pyridyl groups of the formula (Ib).

In a preferred embodiment, the aryl halides of the formula (II) are selected from anilines (R$^1$=amino); 2-bromoaniline and 2-bromo-4-fluoroaniline are particularly preferred.

In an alternative preferred embodiment of the invention, the aryl halides of the formula (II) are selected from acetanilides (R$^1$═CH$_3$—(CO)—NH—); 2-bromoacetanilide and 2-bromo-4-fluoroacetanilide are particularly preferred.

In a further preferred embodiment of the invention, the aryl halides of the formula (II) are selected from the group consisting of N-(2-bromo-4-fluorophenyl)acetamide, N-(2-chloro-4-fluorophenyl)acetamide, N-(2-bromophenyl)acetamide, N-(2-chlorophenyl)acetamide, N-(2-chlorophenyl)-3-oxobutanamide, N-(2-bromophenyl)-3-oxobutanamide, N-(2-chloro-4-fluorophenyl)-3-oxobutanamide, N-(2-bromo-4-fluorophenyl)-3-oxobutanamide, 2-bromo-N-(prop-2-ylidene)aniline, 2-chloro-N-(prop-2-ylidene)aniline, 2-bromo-4-fluoro-N-(prop-2-ylidene)aniline, 2-chloro-4-fluoro-N-(prop-2-ylidene)aniline.

In a further preferred embodiment of the invention, the aryl halides of the formula (II) are selected from pyrazolyl- or pyridylanilides (R$^1$═R$^2$—(CO)—NH—), which contain pyrazolyl groups of the formula (Ia) with R$^5$═CHF$_2$ or pyridyl groups of the formula (Ib).

(Ia)

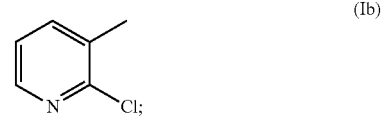

(Ib)

N-(2-bromophenyl)-3-(difluoromethyl)-1-methyl-1H-pyrazole-4-carboxamide, N-(2-bromo-4-fluorophenyl)-3-(difluoromethyl)-1-methyl-1H-pyrazole-4-carboxamide and N-(2-bromophenyl)-2-chloronicotinamide are particularly preferred.

The tetraarylborates according to the invention are compounds of the formula (III)

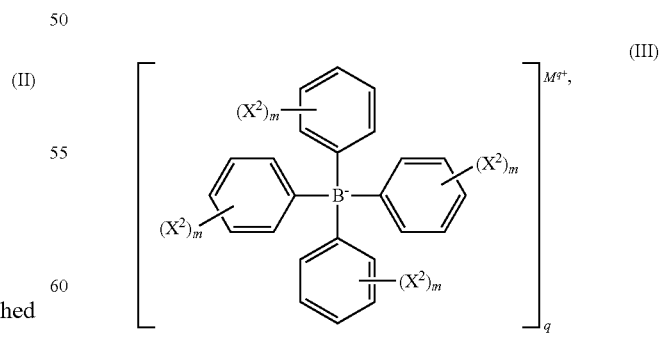

(III)

in which
X$^2$ is selected from halogen atoms and linear or branched C$_{1-12}$-alkyl groups, preferably from halogen atoms, and X$^2$ is particularly preferably chlorine or fluorine;

m is 1, 2, 3, 4 or 5, preferably 1, 2 or 3, particularly preferably 2 or 3,

M is a cation which, for example, is selected from the group consisting of ammonium (q=1), alkali metals, e.g. lithium, sodium and potassium (q=1), alkaline earth metals, e.g. magnesium, calcium or barium (q=2), or complex alkaline earth metal halides, such as, for example, $[MgCl]^+$, $[MgBr]^+$, $[CaBr]^+$, $[CaCl]^+$ (q=1).

In a preferred embodiment of the invention, the tetraarylborate of the formula (III) is selected from the group consisting of sodium tetrakis(3,4-dichlorophenyl)borate, potassium tetrakis(3,4-dichlorophenyl)borate, sodium tetrakis(4-chlorophenyl)borate, potassium tetrakis(4-chlorophenyl)borate, sodium tetrakis(3,4,5-trifluorophenyl)borate, potassium tetrakis(3,4,5-trifluorophenyl)borate.

In the context of the present invention, particularly preferred tetraarylborates are sodium tetrakis(3,4-dichlorophenyl)borate, sodium tetrakis(3,4,5-trifluorophenyl)borate, sodium tetrakis(4-chlorophenyl)borate.

The tetraarylborates can be prepared, for example according to the synthesis method in J. Serwatoski et al. *Tetrahedron Letters* 2003, 44, 7329.

The coupling of the tetraarylborates of the formula (III) to the aryl halides of the formula (II) preferably takes place in the presence of at least one solvent which, for example, is selected from the group consisting of water, aliphatic ethers, optionally halogenated aromatic or aliphatic hydrocarbons, alcohols, esters, aromatic or aliphatic nitriles and dipolar aprotic solvents, such as dialkyl sulphoxides, N,N-dialkylamides of aliphatic carboxylic acids or alkylated lactams.

Solvents which are selected from the group consisting of THF, dioxane, diethyl ether, diglyme, methyl tert-butyl ether (MTBE), tert-amyl methyl ether (TAME), dimethyl ether (DME), 2-methyl-THF, acetonitrile, butyronitrile, toluene, xylenes, mesitylene, anisole, ethyl acetate, isopropyl acetate, methanol, ethanol, propanol, butanol, ethylene glycol, ethylene carbonate, propylene carbonate, N,N-dimethylacetamide, N,N-dimethylformamide, N-methylpyrrolidone, water and mixtures of these are particularly preferred.

Mixtures of toluene, THF or dioxane and water are very particularly preferred.

It was also observed that the addition of small amounts (up to 20% of the solvent) of water to the organic solvents contributes to substantial suppression of the competing homocoupling reaction.

Owing to the solubilities of the starting materials and of the resulting products, however, it is generally not possible to dispense completely with the presence of an organic (nonpolar) solvent. The organic solvents are therefore preferably used as cosolvents.

The solvent mixtures according to the invention may contain between 0.1 and 95% by volume and preferably between 1 and 60% by volume of water, based on the mixture of water and the organic solvent.

Since an acid is formed in the reaction, it is advantageous to trap the resulting acid by addition of a base. The base may either be present from the beginning or may be metered in continuously during the reaction (semibatch process).

Bases suitable according to the present invention are, for example, primary, secondary and tertiary amines, such as, for example, alkylamines, dialkylamines, trialkylamines, which may be alicyclic or open-chain; alkali metal and alkaline earth metal salts of aliphatic and/or aromatic carboxylic acids, such as acetates, propionates or benzoates; alkali metal and alkaline earth metal carbonates, bicarbonates, phosphates, hydrogen phosphates and/or hydroxides; and metal alkoxides, in particular alkali metal or alkaline earth metal alkoxides, such as, for example, sodium methanolate, potassium methanolate, sodium ethanolate, magnesium methanolate, calcium ethanolate, sodium tert-butylate, potassium tert-butylate or alkali metal isoamylates. The base is preferably a carbonate, hydroxide or phosphate of lithium, sodium, potassium, calcium, magnesium or caesium. NaOH, KOH, potassium carbonate and sodium carbonate are particularly preferred.

The Suzuki coupling takes place in the presence of palladium catalysts. In principle, all palladium catalysts described in the prior art in connection with Suzuki couplings can be used.

Preferably used palladium catalysts are those which are selected from the following groups (a) to (c):

a) palladium complexes comprising palladium in the oxidation state zero and phosphine ligands of the general formula $PR'_3$, in which R', independently of one another, is selected from the group consisting of $C_{1-6}$-alkyl, $C_{3-5}$-cycloalkyl and $C_{6-12}$-aryl or phosphinoferrocene ligands;

b) palladium salts in the presence of phosphine ligands of the general formula $PR'_3$, in which R', independently of one another, is selected from the group consisting of $C_{1-6}$-alkyl, $C_{3-5}$-cycloalkyl and $C_{6-12}$-aryl or in the presence of phosphinoferrocene ligands;

c) palladium metal which is optionally applied to a support, it optionally being possible to add phosphine ligands of the general formula $PR'_3$, in which R', independently of one another, is selected from the group consisting of $C_{1-6}$-alkyl, $C_{3-5}$-cycloalkyl and $C_{6-12}$-aryl or phosphinoferrocene ligands.

In a preferred embodiment of the invention, the palladium catalyst of category (a) is selected from the group consisting of tetrakis(triphenylphosphine)palladium, tetrakis(tri-tert-butylphosphine)palladium, adamant-1-yl(adamant-2-yl)butylphosphinepalladium, biphenyl-2-yl(di-tert-butyl)phosphinepalladium or 1,1-bis(di-tert-butylphosphino)ferrocenepalladium, pentaphenyl(di-tert-butylphosphino)ferrocenepalladium, 1,3-bis(di-tert-butylphosphinomethylene)phenylpalladium.

In a further preferred embodiment of the invention, the palladium catalyst of category (b) is selected from the group consisting of palladium chloride, palladium acetate or bisacetonitrilepalladium chloride, palladium(II)dibenzylideneacetone, bisacetylacetonatepalladium.

The palladium catalysts used are as a rule produced in situ from at least one palladium(II) salt or a palladium(0) compound and the corresponding phosphine ligands. However, they may also be used directly as a palladium(0) compound without the initial catalytic activity being reduced thereby.

Suitable palladium sources are, for example, selected from the group consisting of palladium trifluoroacetate, palladium fluoroacetylacetonate, palladium chloride, palladium acetate, $Pd(OCOCH_2CH_3)_2$, $Pd(OH)_2$, $PdBr_2$, bisacetylacetonatepalladium, $Pd(NO_3)_2$, palladiumdibenzylideneacetone, $Pd_2dba_3$, (dba=dibenzylideneacetone), $Pd(CH_3CN)_2Cl_2$, $Pd(PhCN)_2Cl_2$, $Li[PdCl_4]$, Pd/C or palladium nanoparticles.

According to the present invention, electron-rich and/or sterically hindered phosphines in combination with the palladium(0) source are preferably used for the coupling of electron-poor borates.

Examples of these are methyldi($C_{3-8}$-alkyl)phosphine or tri($C_{3-8}$-alkyl)phosphine ligands branched in the alkyl moiety or salts thereof, particularly preferably of methyldi(tert-butyl)phosphine and tri(tert-butyl)phosphine. Further examples are 1,3-bis(di-tert-butylphosphinomethylene)phenyl, adamant-1-yl(adamant-2-yl)butylphosphine, biphenyl-2-yl(di-tert-butyl)phosphine, 1,1-bis(di-tert-butylphosphino)ferrocene, 1,3-bis(di-tert-butylphosphinomethylene)phenyl, pentaphenyl(di-tert-butylphosphino)ferrocene.

The combination of tri(tert-butyl)phosphine with $Pd_2dba_3$ has proved particularly advantageous with regard to reactivity and formation of homocoupling products.

The trialkylphosphine can also be used as a trialkylphosphonium salt, such as, for example, as tetrafluoroborate (*Org. Lett.* 2001, 3, 4295), perchlorate or hydrogen sulphate and liberated therefrom in situ by a base.

The molar ratio of palladium to the phosphine ligand or phosphinoferrocenyl ligand should be between 4:1 and 1:50 and is preferably between 1:1 and 1:5, particularly preferably between 1:1 and 1:2.

In a preferred embodiment of the invention, the palladium catalyst of category (b) contains 6 to 60 equivalents of triphenylphosphine or tri-tert-butylphosphine per equivalent of palladium salt.

According to the invention, however, $Pd[P(tert-But)_3]_2$ can also be used directly, the preparation of which is described in *JACS* 1976, 98, 5850; *JACS* 1977, 99, 2134 and *JACS* 2001, 123, 2719.

When carrying out the reaction, the catalyst system (Pd+ligand) can be added together or separately, either at room temperature or at elevated temperature. The system can be prepared separately shortly before the procedure by combining a Pd salt and the ligand or can be purchased in crystalline form. It is also possible to add first the ligand and then the palladium salt directly to the batch (in situ process).

According to the present invention, the aryl halides of the formula (II) and the tetraarylborates of the formula (III) are used in the ratio of 4:1, preferably in the ratio 3:1 (II:III). Alternatively, however, one of the two components (II or III), preferably the tetraarylborate (III), can also be used in excess. It is also possible to carry out the reaction with controlled metering, one of the two reaction components being metered in slowly during the reaction. Preferably, a solution of the tetraarylborate (III) is metered in for this purpose while the aryl halide (II), the catalyst and optionally the base are initially introduced. It was observed that this procedure according to the invention reduces the formation of polychlorinated biphenyls, which are products of the homocoupling.

The reaction is carried out in general at a temperature of 20 to 200° C., preferably of 40 to 100° C., particularly preferably of 60 to 90° C., and at a pressure up to 100 bar, preferably at a pressure between atmospheric pressure and 40 bar.

The reaction is preferably effected in the absence of atmospheric oxygen under an inert gas atmosphere, such as, for example, under an argon or nitrogen atmosphere.

Owing to the catalyst activities and stabilities, it is possible with the process according to the invention to use extremely small amounts of catalyst, so that the catalyst costs do not constitute a limit for the corresponding process in comparison with the known Suzuki reactions.

In the process according to the invention, 0.001 to 10.0 mol %, preferably 0.005 to 3.0 mol %, particularly preferably 0.01 to 1.0 mol %, of the palladium catalyst—based on the aryl halide of the formula (II)—are used.

Owing to the small amounts of catalyst, the catalyst can remain in the end product in most cases. Alternatively, however, purification of the biaryls obtained can also be effected by filtration, for example over celite.

The following examples serve for illustrating the process according to the invention without limiting it thereto:

SYNTHESIS EXAMPLES

Example 1

Coupling of N-(2-bromo-4-fluorophenyl)acetamide to sodium tetrakis(3,4-dichlorophenyl)borate in the presence of biphenyl-2-yl(di-tert-butyl)phosphine 96 mg [414 µmol] of N-(2-bromo-4-fluorophenyl)acetamide, 71.6 mg [116 µmol] of sodium tetrakis(3,4-dichlorophenyl)borate and 91.3 mg [861 µmol] of sodium carbonate are initially introduced in 0.8 ml of toluene and 0.2 ml of water in the absence of oxygen. 4.76 mg [16 µmol] of biphenyl-2-yl(di-tert-butyl)phosphine (standard solution in toluene) and 9.4 mg [10 µmol] of $Pd_2dba_3$ are added to this mixture. The reaction mixture is stirred for 19 hours at 82° C. After the end of the reaction (HPLC check), the reaction mixture is cooled to RT, 2 ml of acetonitrile are added and filtration is then effected over a nylon filter (pore size 0.45 µm). The HPLC analysis of the mixture gave the following ratio: N-(3',4'-dichloro-5-fluorobiphenyl-2-yl)acetamide:3,3',4,4'-tetrachlorobiphenyl:N-(2-bromo-4-fluorophenyl)acetamide=99.5:0.5:0.

Example 2

Coupling of N-(2-bromo-4-fluorophenyl)acetamide to sodium tetrakis(3,4-dichlorophenyl)borate in the presence of tri(tert-butyl)phosphine 95.7 mg [412 µmol] of N-(2-bromo-4-fluorophenyl)acetamide, 69.2 mg [112 µmol] of sodium tetrakis(3,4-dichlorophenyl)borate and 94.3 mg [890 µmol] of sodium carbonate are initially introduced in 0.8 ml of toluene and 0.2 ml of water in the absence of oxygen. 3.16 mg [16 µmol] of tri(tert-butyl)phosphine (standard solution in toluene) and 16.4 mg [18 µmol] of $Pd_2dba_3$ are added to this mixture. The reaction mixture is stirred for 19 hours at 82° C. After the end of the reaction (HPLC check), the reaction mixture is cooled to RT, 2 ml of acetonitrile are added and filtration is then effected over a nylon filter (pore size 0.45 µm). The HPLC analysis of the mixture gave the following ratio: N-(3',4'-dichloro-5-fluorobiphenyl-2-yl)acetamide:3,3',4,4'-tetrachlorobiphenyl:N-(2-bromo-4-fluorophenyl)acetamide=96.7:1.15:2.15.

Example 3

Coupling of N-(2-bromo-4-fluorophenyl)acetamide to sodium tetrakis(3,4-dichlorophenyl)borate in the presence of 1,1-bis(di-tert-butylphosphino)ferrocene 102.1 mg [440 µmol] of N-(2-bromo-4-fluorophenyl)acetamide, 65.3 mg [106 µmol] of sodium tetrakis(3,4-dichlorophenyl)borate and 100.5 mg [948 µmol] of sodium carbonate are initially introduced in 0.8 ml of toluene and 0.2 ml of water in the absence of oxygen. 6.89 mg [14 µmol] of 1,1-bis(di-tert-butylphosphino)ferrocene (standard solution in toluene) and 10.1 mg [11 µmol] of $Pd_2dba_3$ are added to this mixture. The reaction mixture is stirred for 19 hours at 82° C. After the end of the reaction (HPLC check), the reaction mixture is cooled to RT, 2 ml of acetonitrile are added and filtration is then effected over a nylon filter (pore size 0.45 µm). The HPLC analysis of the mixture gave the following ratio: N-(3',4'-dichloro-5-fluorobiphenyl-2-yl)acetamide:3, 3',4,4'-tetrachlorobiphenyl:N-(2-bromo-4-fluorophenyl)acetamide=94.21:0.64:5.15.

Example 4

Coupling of N-(2-bromo-4-fluorophenyl)acetamide to sodium tetrakis(3,4-dichlorophenyl)borate in the presence of 1,3-bis(di-tert-butylphosphinomethylene)phenyl 96 mg [413 μmol] of N-(2-bromo-4-fluorophenyl)acetamide, 85.1 mg [0.137 mmol] of sodium tetrakis(3,4-dichlorophenyl)borate and 92.6 mg [873 μmol] of sodium carbonate are initially introduced in 0.8 ml of toluene and 0.2 ml of water in the absence of oxygen. 6.68 mg [16.9 μmol] of 1,3-bis(di-tert-butylphosphinomethylene)phenyl (standard solution in toluene) and 8.71 mg [9.5 μmol] of $Pd_2dba_3$ are added to this mixture. The reaction mixture is stirred for 19 hours at 82° C. After the end of the reaction (HPLC check), the reaction mixture is cooled to RT, 2 ml of acetonitrile are added and filtration is then effected over a nylon filter (pore size 0.45 μm). The HPLC analysis of the mixture gave the following ratio: N-(3',4'-dichloro-5-fluorobiphenyl-2-yl)acetamide:3,3',4,4'-tetrachlorobiphenyl:N-(2-bromo-4-fluorophenyl)acetamide=99.3:0.70:0.

Example 5

Coupling of N-(2-bromo-4-fluorophenyl)acetamide to sodium tetrakis(3,4-dichlorophenyl)borate in the presence of 1,2,3,4,5-pentaphenyl-1'-(di-tert-butylphosphino)ferrocene 104.8 mg [452 μmol] of N-(2-bromo-4-fluorophenyl)acetamide, 74.2 mg [120 μmol] of sodium tetrakis(3,4-dichlorophenyl)borate and 90.9 mg [857 μmol] of sodium carbonate are initially introduced in 0.8 ml of toluene and 0.2 ml of water in the absence of oxygen. 13.79 mg [19.4 μmol] of 1,2,3,4,5-pentaphenyl-1'-(di-tert-butylphosphino)ferrocene (standard solution in toluene) and 8.60 mg [9.4 μmol] of $Pd_2dba_3$ are added to this mixture. The reaction mixture is stirred for 19 hours at 82° C. After the end of the reaction (HPLC check), the reaction mixture is cooled to RT, 2 ml of acetonitrile are added and filtration is then effected over a nylon filter (pore size 0.45 μm). The HPLC analysis of the mixture gave the following ratio: N-(3',4'-dichloro-5-fluorobiphenyl-2-yl)acetamide:3,3',4,4'-tetrachlorobiphenyl:N-(2-bromo-4-fluorophenyl)acetamide=97.96:1.31:0.73.

Example 6

Coupling of N-(2-bromo-4-fluorophenyl)acetamide to sodium tetrakis(3,4,5-trifluorophenyl)borate in the presence of biphenyl-2-yl(di-tert-butyl)phosphine 104.1 mg [449 μmol] of N-(2-bromo-4-fluorophenyl)acetamide, 59.0 mg [106 μmol] of sodium tetrakis(3,4,5-trifluorophenyl)borate and 111.3 mg [1050 μmol] of sodium carbonate are initially introduced in 0.8 ml of toluene and 0.2 ml of water in the absence of oxygen. 4.55 mg [15.3 μmol] of biphenyl-2-yl(di-tert-butyl)phosphine (standard solution in toluene) and 10.6 mg [11.7 μmol] of $Pd_2dba_3$ are added to this mixture. The reaction mixture is stirred for 65 hours at 82° C. After the end of the reaction (HPLC check), the reaction mixture is cooled to RT, 2 ml of acetonitrile are added and filtration is then effected over a nylon filter (pore size 0.45 μm). The HPLC analysis of the mixture gave the following ratio: N-(3',4',5'-trifluoro-5-fluorobiphenyl)acetamide:3,3',4,4',5,5'-hexafluorobiphenyl:N-(2-bromo-4-fluorophenyl)acetamide=90.62:1.48:7.90.

Example 7

Coupling of N-(2-bromo-4-fluorophenyl)acetamide to sodium tetrakis(3,4,5-trifluorophenyl)borate in the presence of tri(tert-butyl)phosphine 102.9 mg [443 μmol] of N-(2-bromo-4-fluorophenyl)acetamide, 70.7 mg [127 μmol] of sodium tetrakis(3,4,5-trifluorophenyl)borate and 100.7 mg [950 μmol] of sodium carbonate are initially introduced in 0.8 ml of toluene and 0.2 ml of water in the absence of oxygen. 3.50 mg [17.3 μmol] of tri(tert-butyl)phosphine (standard solution in toluene) and 6.90 mg [7.5 μmol] of $Pd_2dba_3$ are added to this mixture. The reaction mixture is stirred for 65 hours at 82° C. After the end of the reaction (HPLC check), the reaction mixture is cooled to RT, 2 ml of acetonitrile are added and filtration is then effected over a nylon filter (pore size 0.45 μm). The HPLC analysis of the mixture gave the following ratio: N-(3',4',5'-trifluoro-5-fluorobiphenyl)acetamide:3,3',4,4',5,5'-hexafluorobiphenyl:N-(2-bromo-4-fluorophenyl)acetamide=96.5:3.5:0.

Example 8

Coupling of N-(2-bromo-4-fluorophenyl)acetamide to sodium tetrakis(3,4,5-trifluorophenyl)borate in the presence of 1,1-bis(di-tert-butylphosphino)ferrocene 106.1 mg [457 μmol] of N-(2-bromo-4-fluorophenyl)acetamide, 66.6 mg [119 μmol] of sodium tetrakis(3,4,5-trifluorophenyl)borate and 87.0 mg [821 μmol] of sodium carbonate are initially introduced in 0.8 ml of toluene and 0.2 ml of water in the absence of oxygen. 8.02 mg [16.9 μmol] of 1,1-bis(di-tert-butylphosphino)ferrocene (standard solution in toluene) and 13 mg [14.2 μmol] of $Pd_2dba_3$ are added to this mixture. The reaction mixture is stirred for 65 hours at 82° C. After the end of the reaction (HPLC check), the reaction mixture is cooled to RT, 2 ml of acetonitrile are added and filtration is then effected over a nylon filter (pore size 0.45 μm). The HPLC analysis of the mixture gave the following ratio: N-(3',4',5'-trifluoro-5-fluorobiphenyl)acetamide:3,3',4,4',5,5'-hexafluorobiphenyl:N-(2-bromo-4-fluorophenyl)acetamide=99.0:1.0:0.

Example 9

Coupling of N-(2-bromo-4-fluorophenyl)acetamide to sodium tetrakis(3,4,5-trifluorophenyl)borate in the presence of 1,2,3,4,5-pentaphenyl-1'-(di-tert-butylphosphino)ferrocene 102.7 mg [443 μmol] of N-(2-bromo-4-fluorophenyl)acetamide, 65.8 mg [118 μmol] of sodium tetrakis(3,4,5-trifluorophenyl)borate and 92.2 mg [870 μmol] of sodium carbonate are initially introduced in 0.8 ml of toluene and 0.2 ml of water in the absence of oxygen. 11.95 mg [16.8 μmol] of 1,2,3,4,5-pentaphenyl-1'-(di-tert-butylphosphino)ferrocene (standard solution in toluene) and 8.1 mg [8.9 μmol] of $Pd_2dba_3$ are added to this mixture. The reaction mixture is stirred for 65 hours at 82° C. After the end of the reaction (HPLC check), the reaction mixture is cooled to RT, 2 ml of acetonitrile are added and filtration is then effected over a nylon filter (pore size 0.45 μm). The HPLC analysis of the mixture gave the following ratio: N-(3',4',5'-trifluoro-5-fluorobiphenyl)acetamide:3,3',4,4',5,5'-hexafluorobiphenyl:N-(2-bromo-4-fluorophenyl)acetamide=98.5:1.5:0.

Example 10

Coupling of N-(2-bromo-4-fluorophenyl)acetamide to sodium tetrakis(3,4,5-trifluorophenyl)borate in the presence of tri(tert-butyl)phosphine 5 g [21.55 mmol] of N-(2-bromo-4-fluorophenyl)acetamide, 3.25 g [5.82 mmol] of sodium tetrakis(3,4,5-trifluorophenyl)borate and 4.57 g [43.1 mmol] of sodium carbonate are initially introduced in 30 ml of toluene and 10 ml of water in the absence of oxygen. A solution of 348 mg [1.724 mmol] of tri(tert-butyl)phosphine and 786 mg [0.858 mmol] of $Pd_2dba_3$ in 10 ml of toluene is added to this mixture. The reaction mixture is stirred for 24 hours at 82° C. The reaction mixture is cooled to RT and 70 ml of toluene and 50 ml of water are then added. The organic phase is filtered off over celite and concentrated on a rotary evaporator. 5.83 g of N-(3',4',5'-trifluoro-5-fluorobiphenyl)acetamide having a GC purity of 69.8% are obtained.

Example 11

Preparation of sodium tetrakis(3,4,5-trifluorophenyl)borate 35 g [166 mmol] of 5-bromo-1,2,3-trifluorobenzene in 100 ml of diethyl ether are added dropwise to a suspension of 4.15 g [171 mmol] of magnesium and 4.74 g [43 mmol] of sodium tetrafluoroborate in 50 ml of diethyl ether in the absence of oxygen in about 2 hours with gentle refluxing. The Grignard reaction starts after about 5% addition of 5-bromo-1,2,3-trifluorobenzene. The reaction mixture is stirred for a further 12 hours at room temperature. The mixture is allowed to run into a solution of 50 g of sodium carbonate in 700 ml of water. After diethyl ether has been distilled off, the aqueous phase is extracted with methyl tert-butyl ether, the combined organic phases are dried with $Na_2SO_4$ and the solvent is removed in vacuo. After washing with a little water and drying, sodium tetrakis(3,4,5-trifluorophenyl)borate was obtained. $^1$H NMR ($CD_3CN$) δ 6.80-6.71 (m, 8H); $^{13}C$ NMR δ 157.4; 150.8; 137.0; 118.1.

The invention claimed is:

1. A process for the preparation of a substituted biphenyl of formula (I)

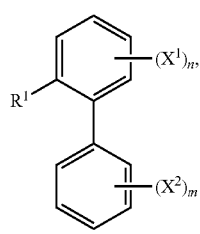

in which
X$^1$ and X$^2$, independently of one another, are halogen atoms or linear or branched $C_{1-12}$-alkyl groups;
n is 0, 1 or 2;
m is 1, 2, 3, 4 or 5;
R$^1$ is selected from the group consisting of amino (NHR$^2$), nitro (NO$_2$), amide groups (R$^2$—(CO)—NH—) and Schiff's bases (R$^3$R$^4$C=N—),
R$^2$, R$^3$ and R$^4$, independently of one another, are linear or branched $C_{1-12}$-alkyl groups or cyclic $C_{3-8}$-alkyl groups, benzyl groups, benzoyl groups, prazolyl groups of formula (Ia), or pyridyl groups of formula (Ib)

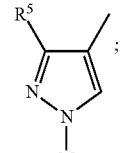

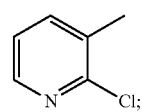

R$^3$ is a linear or branched $C_{1-12}$-alkyl group or a $C_{1-6}$-haloalkyl group having 1 to 6 halogen atoms,
comprising reacting an aryl halide of formula (II)

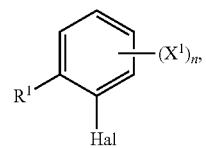

in which
Hal is selected from the group consisting of bromine, chlorine and iodine; and
R$^1$, X$^1$ and n are as defined above,
in the presence of a base and a palladium catalyst in a solvent,
with a tetraarylborate of formula (III)

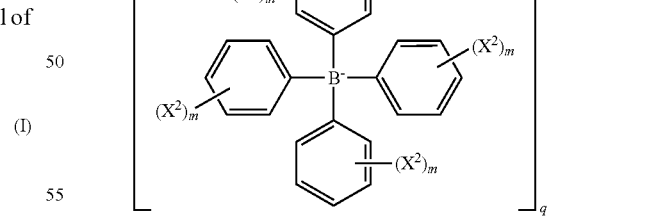

in which
X$^2$ and m are as defined above, and
M$^{q+}$ is a cation selected from the group consisting of ammonium (q=1), alkali metal (q=1) and alkaline earth metal (q=2).

2. The process according to claim 1, wherein
X$^1$ is 5-fluoro;
X$^2$ is 3/4-chloro;
n is 1;
m is 2;

R¹ is selected from the group consisting of amino ($NH_2$), nitro ($NO_2$), amide groups ($R^2$—(CO)—NH—) and Schiff's bases ($R^3R^4C=N—$), R², R³ and R⁴, independently of one another, are linear or branched $C_{1-12}$-alkyl groups or cyclic $C_{3-8}$-alkyl groups.

3. The process according to claim 1, wherein
   X¹ is hydrogen;
   X² is 3,4,5-fluoro;
   n is 1;
   m is 3;
   R¹ is selected from the group consisting of amino ($NH_2$), nitro ($NO_2$), amide groups ($R^2$—(CO)—NH—) and Schiff's bases ($R^3R^4C=N—$),
   R², R³ and R⁴, independently of one another, are linear or branched $C_{1-12}$-alkyl groups or cyclic $C_{3-8}$-alkyl groups.

4. The process according to claim 1, wherein the aryl halide of formula (II) is selected from the group consisting of N—(2-bromo-4-fluorophenyl)acetamide, N-(2-chloro-4-fluorophenyl)acetamide, N-(2-bromophenyl)acetamide, N-(2-chlorophenyl)acetamide, N-(2-chlorophenyl)-3-oxobutanamide, N-(2-bromophenyl)-3-oxobutanamide, N-(2-chloro-4-fluorophenyl)-3-oxobutanamide, N-(2-bromo-4-fluorophenyl)-3-oxobutanamide, 2-bromo-N-(prop-2-ylidene)aniline, 2-chloro-N-(prop-2-ylidene)aniline, 2-bromo-4-fluoro-N-(prop-2-ylidene)aniline, and 2-chloro-4-fluoro-N-(prop-2-ylidene)aniline.

5. The process according to any of claims 1 to 4, wherein the tetraarylborate of formula (III) is selected from the group consisting of sodium tetrakis(3,4-dichlorophenyl)borate, potassium tetrakis(3,4-dichlorophenyl)borate, sodium tetrakis(4-chlorophenyl)borate, potassium tetrakis(4-chlorophenyl)borate, sodium tetrakis(3,4,5-trifluorophenyl)borate, and potassium tetrakis(3,4,5-trifluorophenyl)borate.

6. The process according to any of claims 1 to 4, wherein the palladium catalyst is
   a) palladium complexes comprising palladium in the oxidation state zero and phosphine ligands of formula $PR'_3$, in which R', independently of one another, is selected from the group consisting of $C_{1-6}$-alkyl, $C_{3-5}$-cycloalkyl and $C_{6-12}$-aryl and phosphinoferrocene ligands;
   b) palladium salts in the presence of phosphine ligands of formula $PR'_3$, in which R', independently of one another, is selected from the group consisting of $C_{1-6}$-alkyl, $C_{3-5}$-cycloalkyl and $C_{6-12}$-aryl, or in the presence of phosphinoferrocene ligands; or
   c) palladium metal which is optionally applied to a support and optionally added phosphine ligands of formula $PR'_3$, in which R', independently of one another, is selected from the group consisting of $C_{1-6}$-alkyl, $C_{3-5}$-cycloalkyl and $C_{6-12}$-aryl and phosphinoferrocene ligands.

7. The process according to claim 6, wherein the palladium catalyst is selected from the group consisting of tetrakis(triphenylphosphine)palladium, tetrakis(tri-tert-butylphosphine)palladium, adamant-1-yl(adamant-2-yl)butylphosphinepalladium, biphenyl-2-yl(di-tert-butyl)phosphinepalladium, 1,1-bis(di-tert-butylphosphino)ferrocenepalladium, pentaphenyl(di-tert-butylphosphino)ferrocenepalladium, and 1,3-bis(di-tert-butylphosphinomethylene)phenylpalladium.

8. The process according to claim 6, wherein the palladium catalyst is selected from the group consisting of palladium chloride, palladium acetate or bisacetonitrilepalladium chloride, palladium(II)dibenzylideneacetone, and bisacetylacetonatepalladium.

9. The process according to claim 1, wherein 0.001 to 10.0 mol % of the palladium catalyst—based on the aryl halide of formula (II)—is used.

10. The process according to any of claims 1 to 4, wherein the reaction is effected at a temperature of 20 to 100° C.

11. The process according to any of claims 1 to 4, wherein the solvent is a mixture of water and at least one organic solvent.

12. The process according to claim 11, the organic solvent is toluene.

13. The process according to claim 5, wherein the palladium catalyst is
   a) palladium complexes comprising palladium in the oxidation state zero and phosphine ligands of formula $PR'_3$, in which R', independently of one another, is selected from the group consisting of $C_{1-6}$-alkyl, $C_{3-5}$-cycloalkyl and $C_{6-12}$-aryl and phosphinoferrocene ligands;
   b) palladium salts in the presence of phosphine ligands of formula $PR'_3$, in which R', independently of one another, is selected from the group consisting of $C_{1-6}$-alkyl, $C_{3-5}$-cycloalkyl and $C_{6-12}$-aryl, or in the presence of phosphinoferrocene ligands; or
   c) palladium metal which is optionally applied to a support and optionally added phosphine ligands of formula $PR'_3$, in which R', independently of one another, is selected from the group consisting of $C_{1-6}$-alkyl, $C_{3-5}$-cycloalkyl and $C_{6-12}$-aryl and phosphinoferrocene ligands.

14. The process according to claim 13, wherein the palladium catalyst is selected from the group consisting of tetrakis(triphenylphosphine)palladium, tetrakis(tri-tert-butylphosphine)palladium, adamant-1-yl(adamant-2-yl)butylphosphinepalladium, biphenyl-2-yl(di-tert-butyl)phosphinepalladium, 1,1-bis(di-tert-butylphosphino)ferrocenepalladium, pentaphenyl(di-tert-butylphosphino)-ferrocenepalladium, and 1,3-bis(di-tert-butylphosphinomethylene)phenylpalladium.

15. The process according to claim 13, wherein the palladium catalyst is selected from the group consisting of palladium chloride, palladium acetate or bisacetonitrilepalladium chloride, palladium(II)dibenzylideneacetone, and bisacetylacetonatepalladium.

* * * * *